United States Patent [19]

Horn et al.

[11] Patent Number: 5,707,812
[45] Date of Patent: Jan. 13, 1998

[54] PURIFICATION OF PLASMID DNA DURING COLUMN CHROMATOGRAPHY

[75] Inventors: Nancy Horn; Greg Budahazi, both of San Diego; Magda Marquet, La Jolla, all of Calif.

[73] Assignee: VICAL Incorporated, San Diego, Calif.

[21] Appl. No.: 692,590

[22] Filed: Aug. 6, 1996

[51] Int. Cl.$^6$ .............................. C12Q 1/68; C12N 15/63; C12N 15/64; C07H 21/04
[52] U.S. Cl. ..................... 435/6; 435/172.1; 435/252.3; 435/320.1; 536/23.1
[58] Field of Search .................... 435/91.1, 172.1, 435/252.3, 320.1, 6; 536/23.1

[56] References Cited

FOREIGN PATENT DOCUMENTS 01-304886  12/1989  Japan .......................... C12N 15/00

OTHER PUBLICATIONS

Vasilevskaya, V., et al. (1995) Collapse of single DNA molecule in poly(ethylene glycol) solutions. J. Chem. Phys. 102(16):6595–6602.
Wilson, R., et al. (1979) Counterion–induced condensation of deoxyribonucleic acid. A light–scattering study. Biochemistry 18(11):2192–2196.
Yoshikawa, K., et al. (1996) Nucleation and growth in single DNA molecules. J. Am. Chem. Soc. 118:929–930.
Zhang, W., et al. (1996) Large electrostatic differences in the binding thermodynamics of a cationic peptide to oligomeric and polymeric DNA. Proc. Natl. Acad. Sci. 93:2511–2516.
Manning, G. (1978) The molecular theory of polyelectrolyte solutions with applications to the electrostatic properties of polynucleotides. Quarterly Reviews of Biophysics II 2:179–246.
Minagawa, K., et al. (1994) Direct observation of the coil–globule transition in DNA molecules. Biopolymers 34:555–558.
Plum, G., et al. (1990) Condensation of DNA by trivalent cations. 2. Effects of cation structure. Biopolymers 30:631–643.
Post, C., et al. (1982) Theory of DNA condensation: collapse versus aggregation. Biopolymers 21:2123–2137.
Schaper, A., et al. (1993) Scanning force microscopy of circular and linear plasmid DNA spread on mica with a quaternary ammonium salt. Nucleic Acids Research 21(25):6004–6009.
Smith, S., et al. (1996) Overstretching B–DNA: The elastic response of individual double–stranded and single–stranded DNA molecules. Science 271:795–799.

Cheng, S., et al. (1975) Condensed states of nucleic acids. II. Effects of moelcular size, base composition, and presence on intercalating agents of the transition of DNA. Biopolymers 14:663–674.
Eickbush, T., et al. (1978) The compaction of DNA helices into either continuous supercoils or folded–fiber rods and toroids. Cell 13:295–306.
Horn, N., et al. (1995) Cancer gene therapy using plasmid DNA: purification of DNA for human clinical trials. Human Gene Therapy 6:565–573.
Lerman, L.S. (1971) A transition to a compact form of DNA in polymer solutions. Proc. Natl. Acad. Sci. 68(8):1886–1890.
Ma, C., et al. (1995) Condensation of plasmids enhanced by Z–DNA conformation of $d(CG)_n$ Inserts. Biochemistry 34:3521–3528.
Ma, C., et al. (1995) Gel electrophoresis measurement of counterion condensation on DNA. Biopolymers 35:211–216.
Akimenko, N.M., et al. (1973) Viscosimetric study on compact form of DNA in water–salt solutions containing polyethylenegycol. FEBS Letters 38(1):61–63.
Al–Shakhshir, R., et al. (1995) Contribution of electrostatic and hydrophobic interactions to the adsorption of proteins by aluminium–containing adjuvants. Vaccine 13(1):41–44.
Anderson, C., et al. (1990) Ion Distributions around DNA and other cylindrical polyions: theroretical descriptions and physical implications. Annu. Rev. Biophys. Chem. 19:423–465.
Anderson, C., et al. (1995) Salt–nucleic acid interactions. Annu. Rev. Phys. Chem. 46:657–700.
Arscott, P., et al. (1990) Condensation of DNA by trivalent cations. 1. Effects of DNA length and topology on the size and shape of condensed particles. Biopolymers 30:619–630.
Arscott, P., et al. (1995) DNA condensation by cobalt hexaammine (III) in alcohol–water mixtures: dielectric constant and other solvent effects. Biopolymers 36:345–364.

*Primary Examiner*—David Guzo
*Assistant Examiner*—William Sandals
*Attorney, Agent, or Firm*—Knobbe, Martens, Olson & Bear, LLP

[57] ABSTRACT

A method for purifying plasmid DNA during column chromatography is provided. A short chain polymeric alcohol, preferably polyethylene glycol, or another DNA condensation agent, is added to a DNA sample prior to column chromatography. The short chain polymeric alcohol or condensation agent promotes improved isolation of plasmid DNA and may be used for large scale purification, particularly for manufacturing plasmid DNA as a biopharmaceutical.

11 Claims, No Drawings

PURIFICATION OF PLASMID DNA DURING COLUMN CHROMATOGRAPHY

FIELD OF THE INVENTION

The present invention relates to methods of purifying plasmid DNA during column chromatography, particularly large scale processing of plasmid DNA suitable for use as a biopharmaceutical in gene therapy and gene immunization.

BACKGROUND OF THE INVENTION

All references cited herein are hereby expressly incorporated by reference. Conventional techniques for the isolation of plasmid DNA from microbial cells are suitable only for small or laboratory scale preparations. One widely used technique involves alkaline cell lysis and acetate neutralization of plasmid-containing bacterial cells which results in the precipitation of host genomic DNA and proteins which are removed by centrifugation. The remaining plasmid DNA is precipitated with ethanol and subjected to cesium chloride/ethidium bromide density gradient centrifugation. Ethidium bromide separates the plasmid DNA into supercoiled, linearized and nicked circular forms and the desired form is collected. Residual ethidium bromide is removed by extraction with butanol and the DNA is precipitated with ethanol. Host cell proteins are removed by repeated phenol extraction, followed by DNA precipitation and repeated isoamyl alcohol/chloroform extractions to remove the phenol.

These common laboratory methods used to isolate and purify plasmid DNA are not suitable for manufacturing processes. Nor are they appropriate for the production of plasmid DNA for use as a biopharmaceutical in gene therapy or gene immunization. Density gradient centrifugations are not scalable; ethidium bromide is a known mutagen; phenol is a harsh chemical; and the process is labor intensive.

Recent efforts to purify recombinant plasmid DNA on a large scale have focused on differential precipitation using polyethylene glycol (PEG) followed by ion exchange and/or size exclusion chromatography. Horn et al., *Hum. Gene Ther.*, 6:565–573, 1995; PCT Application No. WO95/21250. The yield of plasmid DNA using this procedure is typically about 50%. PCT Application No. WO96/02658 discloses large scale plasmid DNA purification comprising bacterial cell lysis, anion exchange chromatography and reverse phase high performance liquid chromatography (HPLC). However, a major problem with the chromatographic purification of plasmid DNA is that the desired product elutes in a broad smear rather than in a sharp peak and appears in the flow-through, thus preventing isolation from lysate components.

Various agents, including polyethylene glycol (PEG), trivalent cations (e.g., hexammine cobalt(III), spermidine), alcohol and polyvinylpyrollidone promote the condensation of DNA molecules from an elongated coiled state to a compacted globular state. Yoshikawa et al., *J. Am. Chem. Soc.*, 118:929–930, 1996; Minagawa et al., *Biopolymers*, 34:555–558, 1994; Arscott et al., *Biopolymers*, 30:619–630, 1990; and Lerman, *Proc. Natl. Acad. Sci. U.S.A.*, 68:1886–1890, 1971. The ability of polyethylene glycol to condense DNA molecules seems to occur at concentrations of 1.9–10.0M PEG (Minagawa et al.), with a transition point being at 6.0M (Yoshikawa et al.). That is, with low concentrations of PEG, DNA molecules stay as elongated coils, while with high concentrations, they contract to small globule conformation (Minagawa et al.).

There is a need for a method of purifying plasmid DNA during column chromatography. This need is especially urgent in the face of the requirement for large scale amounts of plasmid DNA that is of sufficient purity to be used as a drug or a vaccine in gene therapy or gene immunization. The present invention satisfies this need.

SUMMARY OF THE INVENTION

One embodiment of the present invention is an improved method of purifying plasmid DNA from a biological mixture using column chromatography, the improvement comprising:

adding polyethylene glycol to the mixture; and chromatographically separating the DNA from the mixture.

Preferably, the polyethylene glycol is added in an amount between about 0.1% and about 4% (w/v); more preferably, the polyethylene glycol is added in amount of about 1% (w/v). In one aspect of this preferred embodiment, the polyethylene glycol has an average molecular weight of about 7,000 to about 9,000; in another aspect the PEG is PEG-8000. This embodiment also includes that the separating step is anion exchange chromatography.

The present invention also provides a method of purifying plasmid DNA from host cell impurities, comprising:

adding polyethylene glycol to a solution containing the plasmid DNA and host cell contaminants in an amount sufficient to cause the plasmid DNA to separate from the host cell impurities during column chromatography; and performing the column chromatography whereby the plasmid DNA is purified from the host cell impurities.

Preferably, the amount of polyethylene glycol is between about 0.1% and about 4% (w/v); more preferably, the polyethylene glycol is added in amount of about 1% (w/v). According to one aspect of this preferred embodiment, the polyethylene glycol has an average molecular weight of about 7,000 to about 9,000; according to another aspect, the PEG is PEG-8000. This embodiment also provides that the column chromatography is anion exchange chromatography.

Another embodiment of the invention is a method of purifying plasmid DNA from lysate contaminants, comprising:

adding a DNA condensation agent to a solution containing the plasmid DNA and lysate contaminants in an amount sufficient to condense the DNA; and passing the solution containing the condensation agent through a chromatography column whereby the plasmid DNA is purified from the lysate contaminants.

Advantageously, the condensation agent is polyethylene glycol, preferably having an average molecular weight of about 7,000 to about 9,000, more preferably, being PEG-8000. Favorably, the amount of polyethylene glycol is between about 0.1% and about 4% (w/v); more favorably, the amount is about 1% (w/v). This embodiment also includes that the chromatography column is an anion exchange chromatography column.

DETAILED DESCRIPTION OF THE PREFERRED EMBODIMENTS

The present invention provides methods for purifying plasmid DNA during column chromatography. A short chain polymeric alcohol, preferably polyethylene glycol, or another DNA condensation agent, is added to a DNA sample prior to column chromatography. The short chain polymeric alcohol, or condensation agent, promotes improved isolation of plasmid DNA and may be used for large scale purification, particularly for manufacturing plasmid DNA as a biopharmaceutical.

A major problem with the chromatographic purification of plasmid DNA from host cell contaminants is that the desired product elutes in a broad smear rather than in a sharp peak and appears in the flow-through, thus preventing isolation of the plasmid DNA from these contaminants. The methods of the present invention solve this problem. In the presence of a short chain polymeric alcohol, such as polyethylene glycol (PEG), or another DNA condensation agent, plasmid DNA elutes in a sharp peak and does not appear in the flow-through, thus facilitating purification and increasing yields.

Without being bound by any particular theory, the uniform binding of plasmid DNA to a chromatography column may result from condensation of DNA in an elongated coiled state to a compacted globular state. Plasmid DNA exists as a mixture of supercoiled, nicked circular, and linearized forms. Upon application of a DNA sample to an ion exchange column, the various plasmid DNA species can be visualized as binding to the chromatographic matrix in a heterogeneous manner and with different relative binding constants. The condensation of elongated coils into compact globules may account for increased binding to the anion exchange matrix in a more homogeneous manner and with similar binding constants. Various DNA condensation agents are accordingly contemplated as facilitating purification of plasmid DNA by the present chromatographic methods.

Another theory that may explain the increased binding of DNA to chromatography columns in the presence of polyethylene glycol is the contribution of hydrophobic interactions to conformational shapes. The disruption of hydrophobic interactions by various agents may allow DNA molecules to assume conformational shapes that facilitate binding to a chromatography matrix in a more consistent manner and with like binding constants. Chemical reagents that mediate hydrophobic interactions are consequently envisioned as also being useful in the present invention.

The use of short chain polymeric alcohols, like polyethylene glycol, and other condensation agents that cause plasmid DNA to act homogeneously for purposes of purification is not limited to ion exchange chromatography. It extends to other chromatographic methods, including size exclusion chromatography, chromatofocusing, affinity chromatography, hydrophobic interaction chromatography, and reversed phase chromatography. Indeed, this use extends broadly to other purification methods, e.g., diafiltration, ultrafiltration, and filtration generally, in which the isolation of plasmid DNA from RNA, proteins and other contaminants is facilitated by causing various plasmid DNA species to act as a class.

The methods of the present invention are capable of providing a number of advantages, including higher product recovery of plasmid DNA. The yield of DNA using these methods can be fully 90% for the chromatography step. Moreover, this invention is adaptable to producing large scale quantities of plasmid DNA with sufficient purity for use in human application.

Plasmid DNA is isolated from components of microbial fermentations in general. It is readily apparent to those skilled in the art that a wide variety of microbial cells are suitable for use in the methods of the present invention, including yeast cells and bacterial cells. A preferred microbial fermentation is a bacterial fermentation. A preferred bacterial fermentation is a fermentation of $E.\ coli$ cells. The microbial fermentation may be grown in any liquid medium that is suitable for growth of the bacteria being utilized.

The DNA plasmid to be purified by the methods of the present invention can be any extrachromosomal DNA molecule. It is readily apparent to those skilled in the art that the plasmids can be virtually any size or character. The plasmids can be high copy number, low copy number, or runaway plasmids. They can contain a range of genetic elements that include selectable genes, polylinkers, origins of replication, promoters, enhancers, leader sequences, polyadenylation sites, and termination sequences. The plasmids can encode human genes of basically any origin, and animal genes, too.

Microbial cells containing the plasmid DNA are first harvested from the fermentation medium to produce a cell paste. Any conventional means to harvest cells from a liquid medium is suitable. Such means include centrifugation, filtration, and sedimentation.

Next is cell lysis. Typically, the cells are resuspended in buffer. We do not recommend enzymatic treatment to weaken any cell wall, because the animal enzymes that must be used may harbor animal viruses that would infect human recipients of any product plasmid DNA obtained by these methods. The cells are instead preferably lysed using dilute base and detergent. The resultant lysate is then acidified to precipitate chromosomal DNA and host proteins.

Cell debris and other impurities are next removed by standard means, such as centrifugation, filtration, or sedimentation. We clarify the resultant supernatant by filtration with diatomaceous earth. Filtration with diatomaceous earth also reduces the concentration of host RNA with respect to the supernatant.

After this, plasmid DNA can be precipitated from the clarified filtrate using a precipitating agent under suitable conditions, collected, and resuspended in a buffer. Next, we precipitate host RNA, proteins, and lipopolysaccharides, as opposed to plasmid DNA, with a precipitating agent under conditions appropriate for this purpose. Finally, the filtrate is collected and plasmid DNA re-precipitated using a precipitating agent under conditions suitable therefor. Column chromatography is next.

The DNA pellet is resuspended in column buffer prior to column chromatography. This buffer contains polyethylene glycol or another DNA condensation agent, either alone or in combination. Typically, the concentration of PEG in the DNA solution is from or about 0.1% and to or about 4% (w/v), preferably about 1% (w/v). If the PEG concentration is less than about 0.1% (w/v), no enhancement of plasmid DNA binding occurs. If the PEG concentration is greater than about 4% (w/v), DNA begins to precipitate out of solution. For PEG-8000, this range of from or about 0.1% to or about 4% corresponds to a molar concentration of $1.7 \times 10^{-4}$M and $6.7 \times 10^{-3}$M.

Plasmid DNA is applied to an anion exchange column equilibrated in the same buffer as the DNA sample. A wide variety of available anion exchange matrices are suitable for use in the present invention, including, but not limited to, those available from POROS Anion Exchange Resins, Qiagen, Toso Haas, Sterogene, Spherodex, Nucleopac, and Pharmacia. The column is washed with several bed volumes of the buffer. The flow-through peak contains virtually no plasmid DNA, indicating nearly complete DNA binding to the column matrix. In contrast, plasmid DNA is present in the flow-through when buffer lacking polyethylene glycol is used.

Plasmid DNA is eluted from the column with a single step salt elution in a buffer containing polyethylene glycol. Column fractions are analyzed for plasmid DNA by agarose gel electrophoresis. Fractions containing plasmid DNA are pooled, precipitated, resuspended and applied to a gel filtration column for further processing. Finally, the column purified DNA is readied for ultimate final formulation, sterile fill, and finish.

The elution profile from the ion exchange column is consistent with different DNA preparations. This success extends to large scale DNA preparations as described in Example 4 below. Thus, reproducible chromatography purifications are achieved when a DNA condensation agent is present in the column buffer.

The use of many DNA condensation agents in the present method is contemplated. Such agents include, but are not limited to, short chain polymeric alcohols having 1 to 4 carbons (e.g., polyethylene glycol), trivalent cations (e.g., hexammine cobalt (III), spermidine), short chain alcohols (e.g., methanol, ethanol, isopropanol) and other polymers (e.g., polyvinylpyrrollidone). Although polyethylene glycol having an average molecular weight of about 7,000 to 9,000 is preferred, and PEG-8000, a polyethylene glycol having an average molecular weight of 8,000, for use in the preferred for use in the present invention, polyethylene glycols having other average molecular weights are also contemplated. These include, for example, PEG-200, PEG-500, PEG-1000, PEG-8000 and PEG-10,000. Suitable choices and amounts of a particular DNA condensation agent for use in the methods described herein can easily be determined by one of ordinary skill in the art, for example, by performing the experiments described in Examples 1–5 and applying scientific methodology to test variables while running controls.

Plasmid DNA was isolated by bacterial cell lysis and column chromatography as described in the following examples.

EXAMPLE 1

Small scale bacterial cell lysis and plasmid recovery

Approximately 50 grams of VCL-1005G/A containing *E. coli* cells were used. The plasmid DNA, VCL-1005G/A, was derived from a pBR322 plasmid. It was approximately 5,000 bp in size. It expressed the gene encoding the kanamycin resistance protein (Tn903). It also encoded the heavy (human HLA-B7 cDNA) and light (chimpanzee β-2 microglobulin cDNA) proteins of a Class 1 Major Histocompatibility Complex termed HLA-B7. These two proteins were expressed on a bi-cistronic mRNA. Eukaryotic cell transcription of this mRNA was dependent on a Rous Sarcoma Virus promoter sequence derived from the 3' Long Terminal Repeat and on a transcription termination/polyadenylation signal sequence derived from the bovine growth hormone gene. Eukaryotic cell expression of the heavy chain was regulated by the 5' cap-dependent protein translation start site. Expression of the light chain was regulated by a Cap Independent Translational Enhancer (CITE) sequence derived from the Encephalomyocarditis Virus. Replication of the plasmid in bacterial cells was controlled by the presence of a bacterial origin of replication.

The cells containing plasmid DNA were resuspended in 300 ml 10 mM Tris-HCl, pH 8.0, 61 mM glucose, 50 mM EDTA. Lysis occurred after the addition of 600 ml 0.2N NaOH, 1% SDS and incubation for 8 minutes. Cellular debris was precipitated with 450 ml 3M potassium acetate, pH 5.0, followed by incubation for 8 minutes. Cellular debris remaining in the lysate was removed by addition of 130 g Celite Hyflo Super cel (flux calcined) (Celite Corp., Lompoc, Calif.), followed by passage through a Celite pre-coated A/E filter disk (Gelman Sciences, Ann Arbor, Mich.) in a Buchner filter under vacuum. The filtrate was passed through a Whatman #4 filter cup to remove any fines, followed by addition of 30% PEG in 1.6M NaCl to a final concentration of 8% PEG to precipitate plasmid DNA. The sample was stirred overnight at 4°–8° C.

Plasmid DNA was collected by centrifugation at 6,000×g for 40 minutes. The pellet was dried for 10 minutes and resuspended in 50 ml TE buffer (10 mM Tris-HCl, pH 8.0, 1 mM EDTA). An equal volume of 5M ammonium acetate was added to the sample, followed by incubation for 15 min on ice. The sample was centrifuged at 2,000×g for 30 min. Plasmid DNA in the supernatant was precipitated by addition of 0.6 volumes of −20° C. isopropanol. After a 2 hour incubation at −20° C., the sample was centrifuged at 2,000×g for 30 minutes. The DNA pellet was dried for 10 minutes and resuspended in 30 ml TE containing 0.15M NaCl.

Plasmid DNA was subjected to anion exchange chromatography in both the presence and absence of PEG as described below.

EXAMPLE 2

Anion exchange chromatography

The 30 ml plasmid DNA sample prepared in accordance with Example 1 was divided in half. To one of the samples was added solid PEG-8000 to a final concentration of 1% (w/v). PEG-8000 was not added to the other 15 ml sample. A Q-SEPHAROSE™ Fast Flow anion exchange column (Pharmacia, Piscataway, N.J.) (5.0×5.0 cm) was pressure packed using the Pharmacia "BioPilot"™ system. The column was equilibrated with either Buffer A (10 mM Tris-HCL, pH. 8.0, 0.7M NaCl, 1 mM EDTA) containing 1% PEG-8000 or with Buffer A. Each 15 ml aliquot was individually loaded into the "BioPilot"™ superloop. After the PEG-containing sample was loaded, a four bed volume wash with buffer A containing PEG was performed. After the control sample (no PEG) was loaded, a four bed volume wash with buffer A was performed. The flow-through peak was collected and retained for analysis on an agarose gel. The DNA was then eluted from the column with four bed volumes of 100% buffer B (10 mM Tris-HCl, pH 8.0, 1 mM EDTA) containing 1% PEG-8000 for the PEG-containing DNA sample or with buffer B (no PEG) for the control DNA sample. 50 ml fractions were collected. Both the flow-through and the fractions eluting after washing with buffer B were analyzed by electrophoresis on a 0.8% agarose gel in the presence of ethidium bromide.

The results indicated that in the presence of 1% PEG-8000, nearly the entire DNA sample was retained on the column as virtually no DNA was present in the flow-through. In contrast, in the absence of PEG-8000, significant leakage of plasmid DNA from the column occurred in which plasmid DNA eluted in the flow-through with various contaminants, indicating that complete binding of DNA was not obtained. The presence of PEG-8000 improved the recovery of plasmid DNA from as little as 20% to generally 80%.

Large scale plasmid purification was performed as described below.

EXAMPLE 3

Large scale bacterial cell lysis and plasmid recovery 500 g VCL-1005G/A containing cells were lysed in an 8 gallon ASME 316T electropolished pressure vessel. The cells were resuspended in 3 liters of 10 mM Tris-HCl, pH 8.0, 6 mM glucose, 50 mM EDTA. Lysis occurred after addition of 6 l of 0.2N NaOH, 1% SDS and incubation for 8 min. Cellular debris was precipitated with 4.5 l of 3M potassium acetate, pH 5.0, followed by incubation for 8 minutes. Cellular debris in the lysate was removed by addition of 675 grams Celite Hyflo Super cel (flux calcined) followed by pressure filtration through a Cuno 8ZP1P 316T stainless cartridge holder containing a 7 cell SP50 cartridge (CUNO, Inc., Meriden, Conn.). The clarified lysate was concentrated and buffer exchange was performed using a 6 FT² PTQK TFF cartridge (Millipore Corp., Bedford, Mass.). A 701S pump (Watson Marlow, Inc., Wilmington, Mass.) was used at a flow rate of 4 l/min (tubing was ⅜" ID Masterflex Pharmed). A six fold volume reduction was followed by diafiltration with two volumes of 10 mM Tris, pH 8.0, 1 mM EDTA.

Plasmid DNA was precipitated from the clarified lysate by addition of 30% PEG-8000 in 1.6M NaCl to a final concentration of 8% overnight at 4° C. with gentle stirring. Plasmid DNA was collected by centrifugation at 6,000×g for 40 minutes using a Jouan KR4 22 centrifuge. The pelleted plasmid DNA was resuspended in 400 ml TE, followed by addition of an equal volume of 5M ammonium acetate. The solution was mixed thoroughly and incubated on ice for 15 minutes, followed by centrifugation at 6,000×g for 20 min. Plasmid DNA was precipitated from the supernatant by addition of 0.6 volume −20° C. Optima grade 2-propanol (Fisher). Following a minimum of 2 hours incubation at −20° C., the precipitated DNA was pelleted at 6,000×g for 20 minutes using a Jouan KR4 22 centrifuge. The pellet was resuspended in 300 ml buffer A containing 1% PEG-8000. The final plasmid DNA concentration as determined by absorbance at 260 nm was about 4 mg/ml and the total amount of nucleic acid was 1.3 grams.

Plasmid DNA was subjected to anion exchange chromatography as described below.

EXAMPLE 4

Anion exchange chromatography

A Pharmacia BPG 100/500 column was pressure packed using the Pharmacia "BioPilot"™ system according to the manufacturer's instructions. Final column dimensions were 10×13 cm resulting in a bed volume of about 1,000 ml. The column was equilibrated with four volumes of buffer A containing 1% PEG-8000 at a flow rate of 35 ml/min. The partially purified plasmid DNA prepared in accordance with Example 3 was passed through a 0.45 μm sterile "Acrodisc" syringe filter (Gelman Sciences) and loaded into the "BioPilot" Superloop. After the sample was loaded onto the column, a three bed volume wash with buffer A was performed. The flow-through peak was collected in a 2 l roller bottle and reserved for gel analysis. The DNA was then eluted from the column with two bed volumes of 100% buffer B containing 1% PEG-8000 for an additional two bed volumes. Fractions (45 ml) were collected after the step to 100% buffer B. Following chromatography, the column was washed with one column volume of 2M NaCl, followed by two column volumes of 1M NaOH. Fractions and flow-through were analyzed by electrophoresis on a 0.8% agarose gel and fractions containing plasmid DNA were pooled and precipitated with 0.6 volume cold 2-propanol.

Similar to the results obtained in Example 2, basically no plasmid DNA was present in the flow-through. Plasmid DNA eluted only after application of the step salt gradient (buffer B).

The plasmid DNA obtained by anion exchange chromatography in the presence of 1% PEG-8000 was further purified by gel filtration chromatography as described below.

EXAMPLE 5

Gel filtration chromatography

A Pharmacia BPG 100/950 gel filtration column was pressure packed with SEPHACRYL™ S-1000 using the "BioPilot" system. Final column dimensions were 10×85 cm for a bed volume of about 6.5 l. The isopropanol-precipitated plasmid DNA from Example 4 was collected by centrifugation at 6,000×g for 20 min, resuspended in 10 mM Tris, pH 8.0, 150 mM NaCl, 1 mM EDTA, and passed through a 0.22 μm sterile cellulose acetate "Acrodisc" syringe filter. The DNA was loaded onto the column. The column running buffer was 10 mM Tris, pH 8.0, 150 mM NaCl, 1 mM EDTA and the flow rate was 8 ml/min. Fractions (45 ml) were collected and analyzed by 0.8% agarose gel electrophoresis. Fractions containing predominantly supercoiled DNA were pooled and precipitated with two volumes of cold ethanol.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A method of purifying plasmid DNA from lysate contaminants comprising:
   (a) preparing a lysate;
   (b) clarifying said lysate to produce a clarified lysate;
   (c) adding a short chain polymeric alcohol to said clarified lysate;
   (d) binding plasmid DNA present in said clarified lysate to a chromatographic matrix by placing said lysate in contact with said chromatographic matrix; and
   (e) eluting said plasmid DNA by placing an eluent in contact with said chromatographic matrix.

2. A method of purifying plasmid DNA from lysate contaminants comprising:
   (a) preparing a lysate;
   (b) clarifying said lysate to produce a clarified lysate;
   (c) adding a short chain polymeric alcohol to said clarified lysate;
   (d) binding plasmid DNA present in said clarified lysate to an ion exchange chromatographic matrix by placing said lysate in contact with said chromatographic matrix; and
   (e) eluting said plasmid DNA by placing an eluent in contact with said chromatographic matrix.

3. The method of claim 2, wherein said ion exchange chromatographic matrix is an anion exchange chromatographic matrix.

4. The method of any one of claims 1, or 2, wherein the yield of plasmid DNA is greater than or equal to 90%.

5. The method of any one of claims 1, or 2, wherein said preparing step is lysis with dilute base and detergent.

6. The method of any one of claims 1, or 2 wherein said clarifying step is filtration with diatomaceous earth.

7. The method of any one of claims 1, or 2, wherein said short chain polymeric alcohol is polyethylene glycol.

8. The method of claim 7, wherein said polyethylene glycol amounted in an amount between about 0.1% and about 4% (w/v).

9. The method of claim 8, wherein said polyethylene glycol is added in an amount of about 1% (w/v).

10. The method of claim 7, wherein said polyethylene glycol has an average molecular weight of about 7,000 to about 9,000.

11. The method of claim 10, wherein said polyethylene glycol is PEG-8000.

* * * * *

UNITED STATES PATENT AND TRADEMARK OFFICE
CERTIFICATE OF CORRECTION

PATENT NO. : 5,707,812
DATED : January 13, 1998
INVENTOR(S) : Horn et al.

It is certified that error appears in the above-identified patent and that said Letters Patent is hereby corrected as shown below:

In column 8, line 56, after glycol, please change "amounted" to --is added--

Signed and Sealed this

Twelfth Day of May, 1998

Attest:

BRUCE LEHMAN

Attesting Officer     Commissioner of Patents and Trademarks